United States Patent [19]

Blackford et al.

[11] Patent Number: 5,351,523
[45] Date of Patent: Oct. 4, 1994

[54] APPARATUS AND PROCESS FOR DETERMINING FILTER EFFICIENCY IN REMOVING COLLOIDAL SUSPENSIONS

[75] Inventors: David B. Blackford, St. Paul; Thomas A. Kerrick, Forrest Lake; Georg Schürmann, Shoreview, all of Minn.; Kevin T. Pate, Beaverton, Oreg.

[73] Assignee: TSI Incorporated, St. Paul, Minn.

[21] Appl. No.: 6,401

[22] Filed: Jan. 21, 1993

[51] Int. Cl.$^5$ ............................................. G01N 15/08
[52] U.S. Cl. ............................................................ 73/38
[58] Field of Search ....................... 73/38, 61.63, 61.71

[56] References Cited

U.S. PATENT DOCUMENTS

| | | | |
|---|---|---|---|
| 2,645,463 | 7/1953 | Stearns | 360/154 |
| 2,819,608 | 1/1958 | McLaren et al. | 73/38 |
| 3,505,876 | 4/1970 | Niebergall | 73/38 |
| 3,726,297 | 4/1973 | Heimann et al. | 137/1 |
| 3,900,290 | 8/1975 | Hornstra | 73/61.73 |
| 4,025,307 | 5/1977 | Randolph | 436/4 |
| 4,164,960 | 8/1979 | Howard | 137/604 |
| 4,382,378 | 5/1983 | Wadsworth et al. | 73/38 |
| 4,405,087 | 9/1983 | Mata-Garza | 239/226 |
| 4,586,825 | 5/1986 | Hayatdavoudi | 366/137 |
| 4,619,136 | 10/1986 | Ortiz | 73/38 |
| 4,729,876 | 3/1988 | Hennessy et al. | 422/103 |
| 4,761,074 | 8/1988 | Kohsaka et al. | 356/37 |
| 4,790,650 | 12/1988 | Keady | 356/37 |
| 4,794,086 | 12/1988 | Kasper et al. | 436/36 |
| 5,059,395 | 10/1991 | Brittenham et al. | 422/73 |
| 5,098,657 | 3/1992 | Blackford et al. | 422/73 |
| 5,178,836 | 1/1993 | Kitamori et al. | 422/73 |
| 5,203,201 | 4/1993 | Gogins | 73/38 |

FOREIGN PATENT DOCUMENTS

| | | | |
|---|---|---|---|
| 0015543 | 1/1985 | Japan | 73/38 |
| 0311145 | 12/1988 | Japan | 73/38 |
| WO88/02116 | 9/1986 | PCT Int'l Appl. | |
| WO90/07259 | 12/1988 | PCT Int'l Appl. | |

Primary Examiner—Hezron E. Williams
Assistant Examiner—Michael J. Brock
Attorney, Agent, or Firm—Frederick W. Niebuhr

[57] ABSTRACT

A system for determining the fractional capture efficiency of filters includes two filters having substantially the same capture efficiency connected in series. A steady, controlled flow of ultrapure water and a colloidal silica suspension is directed through both filters, with respective stages of the flow upstream of the upstream filter, between the filters and downstream of the downstream filter, directed to respective non-volatile residue monitors. Each residue monitor produces a digital output representing the non-volatile residue concentration at its respective stage. A microprocessor receives the digital outputs and generates respective residue values indicating residue concentration in parts per billion. The three residue values are used to characterize the residue by proportion of the colloidal silica suspension to other residue components, and to calculate filter capture efficiency with respect to the colloidal silica. In an alternative embodiment, a valve selectively, individually and alternatively directs each one of the flow stages to a single non-volatile residue monitor. As a further alternative, when the concentration of dissolved impurities is known to be small as compared to the colloidal silica concentration, filter efficiency can be determined using a single filter and two non-volatile residue monitors.

20 Claims, 5 Drawing Sheets

APPARATUS AND PROCESS FOR DETERMINING FILTER EFFICIENCY IN REMOVING COLLOIDAL SUSPENSIONS

BACKGROUND OF THE INVENTION

This invention relates to the testing of filters designed for removing colloidal suspensions, and more particularly to a system employing non-volatile residue monitoring devices to determine the capture efficiency of such filters.

The ability to detect colloidal silica, including colloidal silica in very fine particulate form (e.g. as small as 2-3 nanometers in diameter), is of critical importance to the semiconductor industry. The fabrication of very large scale integrated (VLSI) circuits involves multiple semiconductor wafer surface processing stages, with each stage typically followed by a washing of the wafer with ultrapure water. Despite the frequency of washings, and the attendant care with which the ultrapure water is monitored, colloidal silica and other impurities can accumulate on the wafer, leading to defects in the resulting semiconductor device. Accordingly, there is a need to monitor the ultrapure water for the presence of colloidal silica and to remove the colloidal silica by filtration. To the extent practicable, it is desirable to filter the colloidal silica and measure colloidal silica concentrations in situ, i.e. within the water stream as the ultrapure water is supplied to the wafer for cleaning or other treatment.

Colloidal silica presents difficulty in this regard, as it penetrates most known filters, particularly when in very fine particulate form. Such colloidal silica cannot be detected by a scanning electron microscope (SEM), but requires a substantially more expensive scanning tunneling microscope. Alternatively, colloidal silica can be detected by atomic absorption spectrometry to measure a total amount or proportion of silica, with conventional means employed to measure dissolved silica, with colloidal silica then being the total silica less the dissolved silica. Thus, despite known approaches for measuring colloidal silica, for determining filter efficiencies, there remains a need for a low cost and reliable system, operable in situ.

Therefore, it is an object of the present invention to provide a system for determining filter efficiency, in terms of colloidal silica removal, through monitoring a steady state flow of a test liquid including a colloidal suspension.

Another object is to provide a system for determining such efficiency, based upon measuring residue concentrations, regardless of whether the residue consists entirely of a colloidal suspension, or includes other components as well, e.g. dissolved impurities.

A further object of the invention is to provide a process for determining filter efficiencies for removing colloidal silica, without requiring any direct measurement of colloidal silica concentrations.

Yet another object is to provide a system employing one or more non-volatile residue monitoring devices to determine the efficiency at which filters remove colloidal silica suspended in a liquid stream passing through the filter.

SUMMARY OF THE INVENTION

To achieve these and other objects, there is provided an apparatus for determining the efficiency of filters in removing a colloidal suspension in a liquid stream. The apparatus includes a supply means for generating a continuous liquid flow of a test liquid containing a residue at a proportion substantially uniform throughout the test liquid. The residue includes a colloidal suspension. A first residue measuring means is provided for determining the proportion of the residue in the test liquid. The measuring means then generates a corresponding first residue value. A first filter removes a portion of the colloidal suspension from the test liquid and thereby provides a first filter output. A second residue measuring means, downstream of the first filter, is used to determine the proportion of the residue in the first filter output, and to generate a corresponding second residue value. A second filter, substantially identical to the first filter and downstream of the first filter, receives the first filter output and removes a portion of the colloidal suspension from the first filter output to provide a second filter output. A third residue measuring means, downstream of the second filter, determines the proportion of the residue in the second filter output and generates a corresponding third residue value. The first, second and third residue values can be employed in combination to calculate the efficiency of the first filter and the second filter, in terms of ability to remove the colloidal suspension.

The preferred residue measuring means are non-volatile residue monitoring devices, which devices have been developed and employed successfully in continuously monitoring the quality of ultrapure water. A non-volatile residue monitor is capable of measuring very low levels of impurity; typical concentrations are in the $\mu g/L$ (parts per billion) or $ng/L$ (parts per trillion) measurement range. An example of such device is described in U.S. Pat. No. 5,098,657 (Blackford et al). Flow restrictive elements are arranged to provide a constant, pressure controlled flow of ultrapure water to an atomizer. At the atomizer the water is dispersed into droplets which later are dried, to provide non-volatile residue particles. A condensation nucleus counter determines the particle concentration, which provides an indication of the purity of the water.

The non-volatile residue monitor does not distinguish between the colloidal suspension and other impurities, e.g. impurities dissolved in the ultrapure water. Nonetheless, the two filtration stations provide three residue values, which are sufficient to calculate the colloidal portion of the residue passing through the filters, as well as the filtration efficiency based on filtering only the colloidal suspension. The first and second filters preferably are sub-micron pore sized filters with a high capture efficiency.

A key factor in the utility of this approach is the ability to produce a test liquid in which the residue, for all practical purposes, consists of the colloidal suspension and dissolved impurities, with the filters trapping a portion of the former but virtually none of the latter. The preferred test liquid is ultrapure water containing a colloidal silica suspension. Unavoidably, some dissolved impurities are present in the water along with the colloidal silica. One approach to providing the test liquid is to generate a steady state flow of ultra-pure water (unavoidably containing at least traces of dissolved impurities), and injecting the colloidal silica at a steady rate into the flow of water. The colloidal silica preferably is comprised of minute particles, e.g. having diameters less than about 20 nanometers. When in this size and provided in sufficient numbers, the colloidal silica particles behave essentially as a non-volatile residue, and thus are detected by non-volatile residue monitoring devices. The proportion of dissolved impurities is preferably less than the proportion of colloidal silica, e.g. about 20 parts per billion at the most, as compared to a permitted range of 20 to 100 parts per billion colloidal silica, by weight.

Advantageously, the first and second filters have virtually the same efficiency in terms of capturing colloidal silica. In this event, relatively straightforward calculations yield the filtration efficiency and the proportion of non-captured dissolved impurities.

A satisfactory alternative to a system employing three non-volatile residue monitors is a system employing a single non-volatile residue monitor in combination with a valve or other device that selectively channels either the initial flow, the first filter output, or the second filter output to the non-volatile residue monitor. The required sampling from among alternative flows yields satisfactory results, since the respective residue proportions remain essentially constant. Thus, the alternative system provides reliable results, despite the disadvantage of providing only one of the residue values at any given moment.

Another aspect of the present invention is a process for determining the capture efficiency of filters, including the following steps:
  (1) producing a liquid flow of a test liquid containing a residue, said residue including a colloidal suspension, the proportion of residue being substantially uniform throughout the test liquid;
  (2) determining the proportion of the residue in the test liquid, and generating a corresponding first residue value;
  (3) using a first filter to remove a portion of the colloidal suspension from the test liquid to produce a first filter output;
  (4) determining the proportion of the residue in the first filter output, and generating a corresponding second residue value;
  (5) using a second filter to remove a portion of the colloidal suspension from the first filter output to produce a second filter output;
  (6) determining the proportion of the residue in the second filter output, and generating a corresponding third residue value; and
  (7) combining the first, second and third residue values to calculate the efficiency of the first filter and the second filter in capturing the colloidal suspension.

When the residue further includes impurities dissolved in the test liquid, the step of combining the residue values further includes calculating the proportion of the impurities in the test liquid.

Preferably, the test liquid flow is produced by injecting colloidal silica at a steady rate into a steady flow of ultrapure water. Sufficient turbulence is provided downstream of the injection, to insure a uniform distribution of the colloidal silica suspension throughout the water. Prior to its injection the colloidal silica can be diluted in ultrapure water. A motorized syringe in fluid communication with the ultrapure water is advantageously loaded with colloidal silica in a form already diluted with ultrapure water. The pre-dilution of the colloidal silica enhances the subsequent mixing action to insure a uniform distribution of the colloidal silica.

Thus, in accordance with the present invention, the efficiency of filters in capturing colloidal silica can be determined using non-volatile residue monitoring devices, despite the fact that such devices do not generate outputs representing colloidal silica concentrations as distinguished from residue concentrations in general. The residue measured need not consist entirely of the colloidal silica, nor must the colloidal silica comprise the majority of the residue. When three such monitoring devices are employed in combination with two filters having a substantially identical capture efficiency, straightforward mathematical relationships for determining capture efficiency are employed in combination with data processing equipment receiving the non-volatile residue monitor outputs, for accurate, continuous and real time measurement of filter capture efficiency. If the dissolved impurities are known to be a smaller percentage (say less than 5%) of the colloidal silica challenge, it is not necessary to have two filters and three monitoring points. A single filter will suffice with residue measurements upstream (A) and downstream (B) the filter. Percentage removal of colloidal silica through an individual filter can now be calculated from $$\left(\frac{A-B}{A}\right) \times 100.$$

IN THE DRAWINGS

For a further appreciation of the above and other features and advantages, reference is made to the following detailed description and to the drawings, in which.

DETAILED DESCRIPTION OF THE PREFERRED EMBODIMENTS

Figure 1:
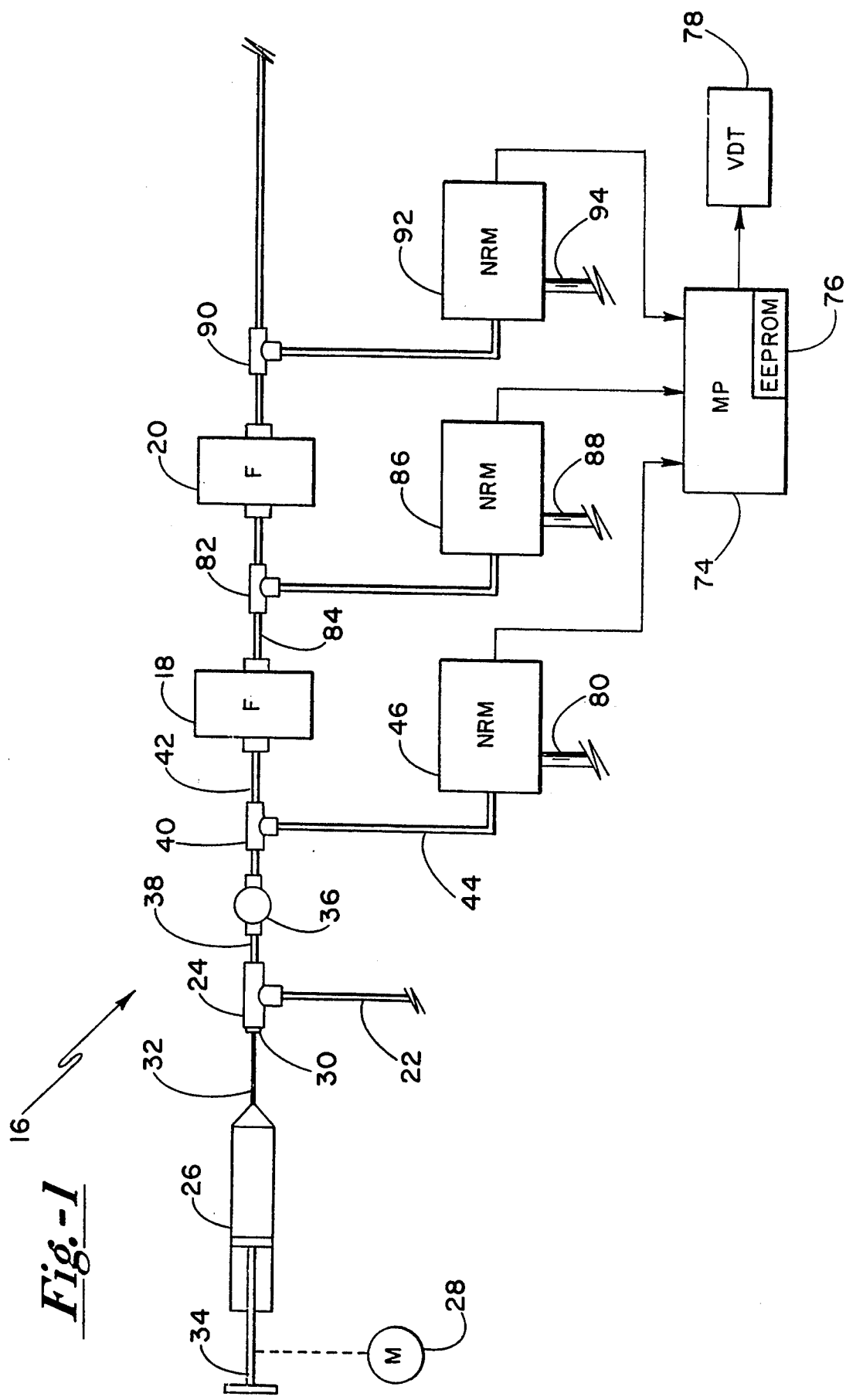
FIG. 1 is a schematic view of a system for determining filter capture efficiencies in accordance with the present invention.

Turning now to the drawings, there is shown in FIG. 1 a system 16 for testing the capture efficiency for a pair of filters 18 and 20. The filters are of the type sold by Filterite Memtec America Corporation of Tinonium, Md., under the brand name "Varafine", and rated at 0.006 microns. Preferably, filters 18 and 20 have identical efficiencies, in terms of removing a suspension, e.g. a colloidal silica suspension, from a stream of ultrapure water or another fluid. Typically, non-volatile residue in the fluid stream does not consist of only colloidal silica suspension. Rather, the residue further includes dissolved impurities, which can include dissolved silica, that travel with the fluid flow through filters 18 and 20, virtually uncaptured.

System 16 is used to test the filtration efficiency of filters 18 and 20, by providing a flow of ultrapure water to the system at a uniform rate, preferably in the range of about 3–4 liters per minute. The rate can be achieved by valves between system 16 and a municipal water supply, with various water treatment components also upstream of the system, e.g. ion exchange beds, carbon and microporous filters, reverse osmosis components, and the like, cooperating to provide ultrapure water based on the municipal water supply.

Ultrapure water is produced using a variety of approaches including deionization, activated carbon filtration, microporous filtration, reverse osmosis, ultraviolet oxidation, ultrafiltration, and distillation. A given water treatment system can advantageously employ several of these approaches in sequence. Regardless of the approaches involved, however, the ultrapure water will contain at least traces of dissolved impurities. Filters 18 and 20, however, capture virtually none of these impurities. Therefore with respect to the dissolved impurities, filters 18 and 20 are assumed to have a captive efficiency of 0 percent.

In any event, the ultrapure water flows through a conduit 22 to a T-fitting 24. A syringe injector 26, precisely controlled by a stepper motor 28, is connected to fitting 24. Syringe 26 injects a colloidal silica dilution into the ultrapure water. To insure against contamination, fitting 24 includes a septum 30 which closes the opening created by withdrawing the syringe, following injection of the colloidal silica. A preferred syringe is available from Beckton-Dickinson & Company of Rutherford, N.J., and identified as "Model No. 9663". A removable hypodermic needle 32 is used in combination with the syringe. The syringe has a capacity of 60 millimeters, and its plunger 34 is controlled by stepper motor 28 to deliver the colloidal silica charge at a preferred rate of about 0.3402 milliliters per minute.

A mixing valve 36 is provided along a conduit 38 downstream of fitting 24. The mixing valve includes a ball valve (not illustrated) within an enlarged portion of the conduit. The ball valve forces the ultrapure water and the colloidal silica dilution to flow along relatively constricted regions between the ball valve and conduit, increasing the fluid velocity and causing turbulence in the flow, just downstream of the valve. Thus, mixing valve 36 insures that the ultrapure water and dilution from syringe 26 are thoroughly mixed to provide a uniform concentration of the colloidal silica throughout the flow.

The water and colloidal silica proceed through conduit 38 to another T-fitting 40 at which the ultrapure water flow is divided. Most of the flow proceeds to filter 18 through a conduit 42, while a fractional portion of the flow (in the range of 70–100 milliliters per minute) proceeds through a conduit 44 to a non-volatile residue monitor 46. The ultrapure water and colloidal silica suspension output of the non-volatile residue monitor 46 is drained as indicated at 80. All conduits and fittings are preferably constructed of perfluoroalkoxy (PFA) to minimize the potential for contamination of the water. PFA is sold, for example, under the brand name Teflon, available from E.I. dupont de Nemours & Co. Inc. Non-volatile residue monitor 46 is available from TSI Incorporated of St. Paul, Minn., sold under the brand name "Liquitrak" and identified as Model Nos. 7760, 7761 or 7770.

Figure 2:
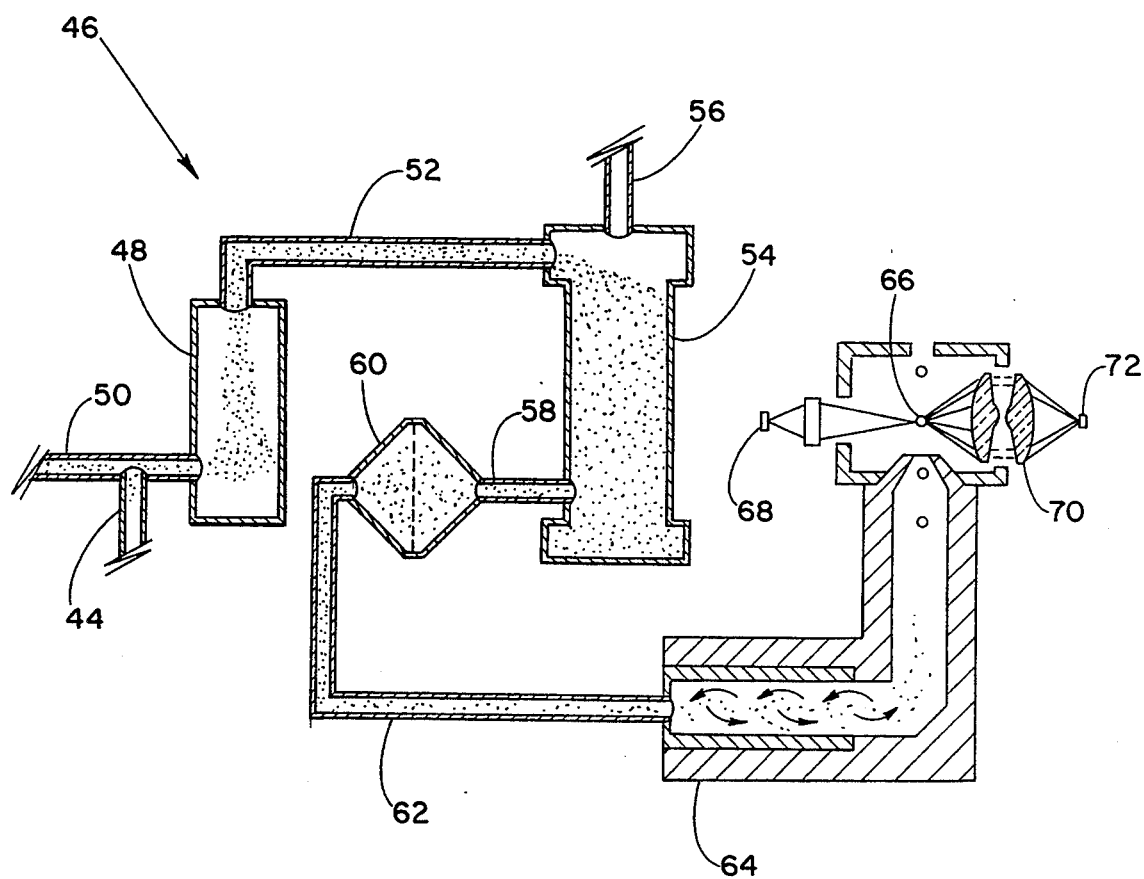
FIG. 2 is a schematic view of a non-volatile residue monitor employed in the system of FIG. 1.

Non-volatile residue monitor 46, shown in more detail in FIG. 2, is used to continuously monitor the concentration of non-volatile residue in the ultrapure water. A small fraction (e.g. about one percent) of the ultrapure water is directed to an atomizer 48 of the monitor. Compressed air or nitrogen also is supplied to the atomizer at a constant flow rate, via a line 50.

Atomizer 48 produces a stream of droplets of the ultrapure water, which travel through a conduit 52 to a drying column 54. Compressed air or nitrogen which has been dried, filtered, and heated to a temperature of about 120 degrees C., is supplied to the drying column through a line 56. The ultrapure water droplets dry rapidly and completely as they travel through drying column 54. Thus, the drying column output is a stream of multiple non-volatile residue particles. Every droplet provided to the drying column from the atomizer yields a residue particle. The cleaner the ultrapure water, the smaller the residue particles.

Non-volatile residue particles leave drying column 56 and progress through a conduit 58 to a diffusion screen or filter 60, where ultra-fine particles (below a predetermined size, e.g. ten nanometers) are removed from the particle stream. More particularly, the ultra-fine particles cling to the walls of filter 60 due to Brownian movement. The remaining particles travel through a conduit 62 to a condensation nucleus counter (CNC) 64.

In the condensation nucleus counter, the particles, supported in a stream of gas, e.g. air or nitrogen, travel through a chamber saturated with a vapor, e.g. N-butyl alcohol. Subsequently, the stream is cooled sufficiently to supersaturate the vapor. The vapor condenses onto the particles to form aerosol droplets substantially larger than the particles themselves. After condensation, the aerosol droplets travel through a viewing region or volume 66 defined by laser energy from a laser diode 68 and associated optics 70. Each droplet causes an optical detector 72 to generate a single electrical pulse. A stream of aerosol droplets, passing through the viewing volume, results in generation of a digital signal, consisting of multiple pulses and representing the concentration of non-volatile residue in the ultrapure water. For a more detailed description of non-volatile residue monitors, reference is made to U.S. Pat. No. 5,098,657 (Blackford et al). For further information on condensation nucleus counters, reference is made to U.S. Pat. No. 4,790,650 (Keady). The Blackford and Keady patents are assigned to the assignee of this application, and incorporated herein by reference.

Condensation nucleus counter 64 detects each aerosol droplet passing through the viewing volume, and thus generates a particle count corresponding to the number of residue particles passing through non-volatile residue monitor 46. The CNC output is an electrical signal, more particularly a digital signal of multiple pulses, one pulse corresponding to each aerosol droplet. The digital signal is provided to a microprocessor 74, including an electrically erasable programmable read only memory (EEPROM) 76. Conversion information stored in EEPROM 76 causes microprocessor 74 to generate an output indicating the concentration of non-volatile residue in parts per billion (ppb). The microprocessor output is provided to a video display terminal 78. Display terminal 78 provides a continuously updated record of residue concentration in the ultrapure water provided to non-volatile residue monitor 46. Returning to FIG. 1, the ultrapure water flow output of non-volatile residue monitor 46 is drained, as indicated at 80.

Most (about 98 percent) of the ultrapure water flow from fitting 40 is directed to filter 18. Filter 18 removes a portion of the colloidal silica from the fluid stream and provides its output to a T-fitting 82 via a conduit 84. At fitting 82, a fractional share of the stream is diverted to a non-volatile residue monitor 86 substantially identical to non-volatile residue monitor 46. The ultrapure water and colloidal silica output of non-volatile residue monitor 86 is drained as indicated at 88. Also, a digital signal representative of the non-volatile residue concentration in the output of filter 18, is provided to microprocessor 74. Consequently, display terminal 78 can provide a continuously updated record of the non-volatile residue concentration in the ultrapure water downstream of filter 18.

Most of the output of filter 18 proceeds through fitting 82 to filter 20, where a further proportion of the silica suspension is removed from the ultrapure water flow. Most of the output of filter 20 proceeds through a fitting 90 for drainage. A fraction of the flow is diverted to provide an input to a non-volatile residue monitor 92, substantially identical to monitors 46 and 86. Non-volatile residue monitor 92 includes an output 94 for draining the ultrapure water and colloidal silica suspension, generates an electrical signal representative of the non-volatile residue concentration, and provides the signal as an input to microprocessor 74.

Figure 3:
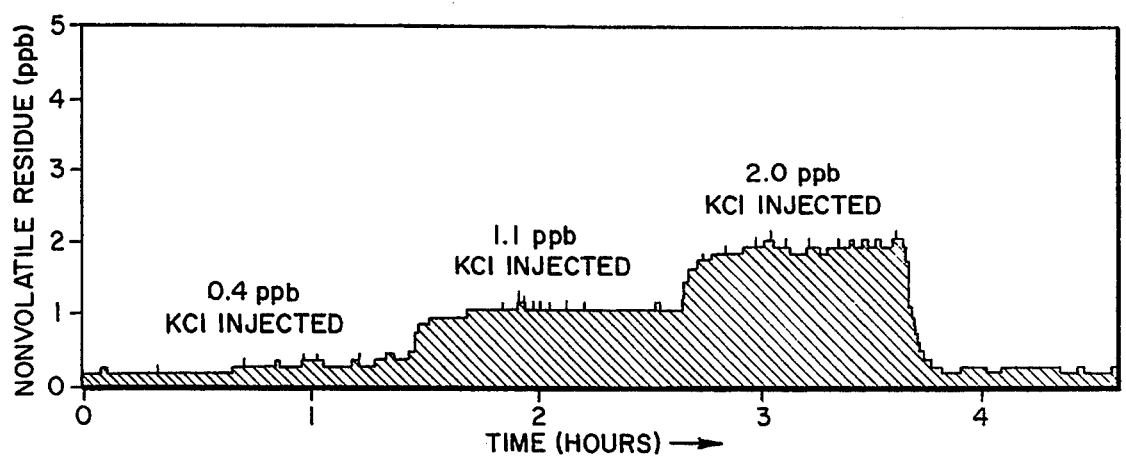
FIGS. 3 and 4 are charts that illustrate potassium chloride concentrations in a liquid stream respectively upstream and downstream of a filter.
Figure 4:
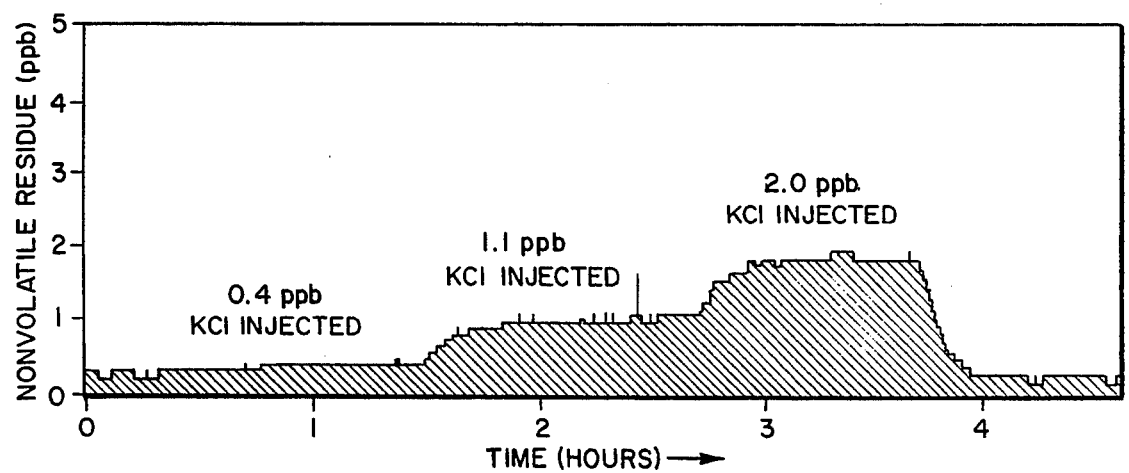

As mentioned previously, filters 18 and 20 are assumed to have a capture efficiency of 0 % with respect to dissolved impurities. FIGS. 3 and 4 are plots of non-volatile residue monitor readings over a time span of approximately five hours, during which potassium chloride (KCl) was injected into an ultrapure water flow, and the combined water and KCl was directed through a filter substantially identical to filters 18 and 20. KCl is a chemical compound that completely dissolves in ultrapure water. FIG. 3 reflects the non-volatile residue monitor readings based on the flow upstream of the filter, while FIG. 4 reflects readings based on the flow downstream of the filter. The upstream and downstream readings are nearly identical, confirming the assumption of 0 % capture efficiency as to potassium chloride. Dissolved impurities other than KCl behave similarly in passing through the filter.

Figure 5:
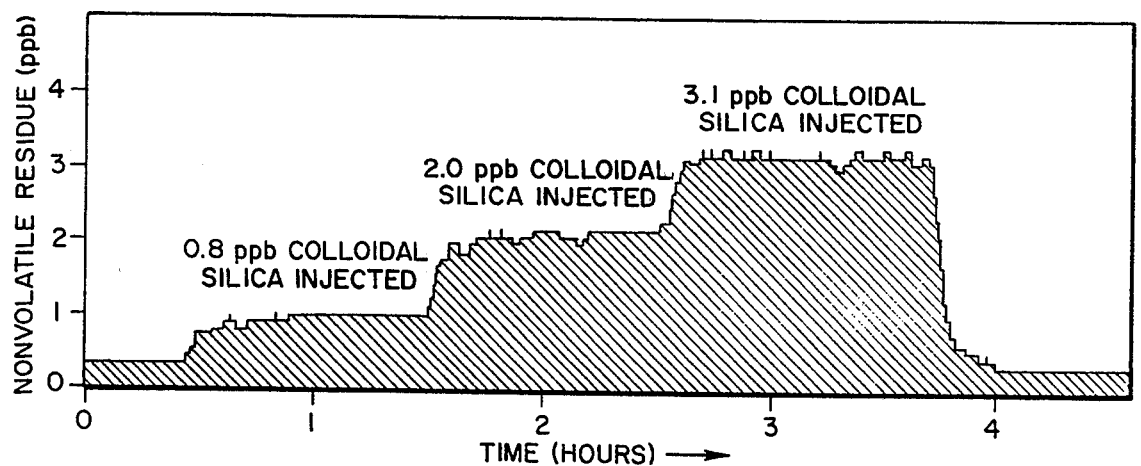
FIGS. 5 and 6 are charts illustrating colloidal silica concentrations in a fluid stream respectively upstream and downstream of the filter.
Figure 6:
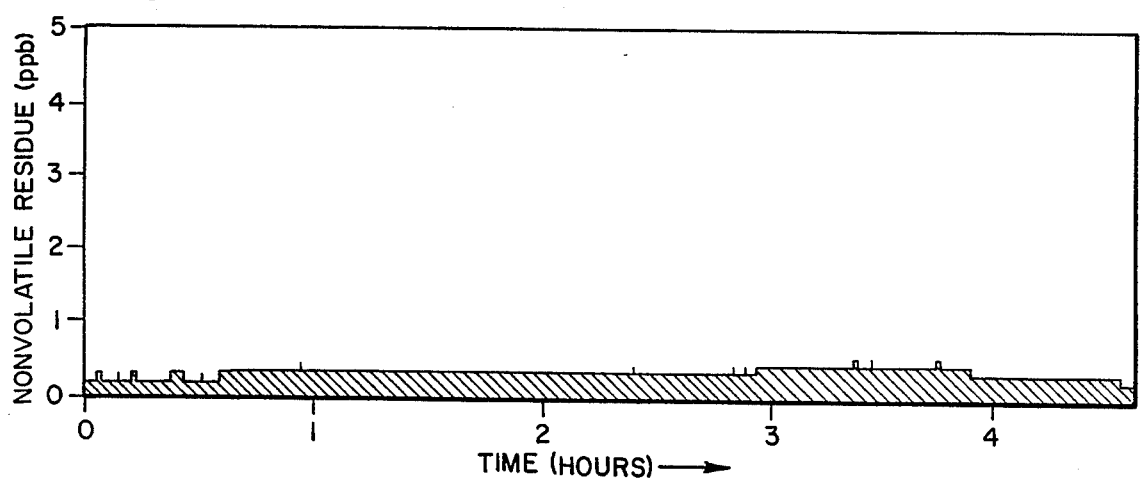

FIGS. 5 and 6 are plots of non-volatile residue monitor readings for a flow of ultrapure water in which a syringe was used to inject a colloidal silica suspension, at rates ranging from 0.8–3.1 ppb. The plots, based on readings respectively upstream and downstream of the filter, illustrate a high efficiency of the filter, in terms of capturing colloidal silica.

System 16 is used to test filtration capture efficiencies, first by providing the uniform flow of ultrapure water as noted above. Then, the colloidal silica suspension is injected using syringe 26.

Reliable testing of filtration efficiency depends upon maintaining a uniform proportion of the colloidal silica during testing. To this end, commercially available grades of colloidal silica are combined with ultrapure water in a series of careful dilutions, to insure accuracy in the proportion of colloidal silica and to facilitate eventual mixture of the colloidal silica into the ultrapure water flow.

Several grades of colloidal silica have been found suitable for filtration efficiency testing, including a 40 % by weight suspension of colloidal silica having a nominal size (individual particle diameter) of 11–14 nanometers, available from Nissan Chemical Corporation Ltd. of Tokyo, Japan under the brand name "Snowtex ST-40". Another suitable grade, also available from Nissan Chemical, is a 20 % by weight suspension having a nominal size of 4–6 nanometers and available under the brand name "Snowtex ST-XS". In both of these products, the colloidal silica is suspended in ultrapure water.

With respect to the 40 % by weight suspension, the dilution procedure begins by adding 45 milliliters of ultrapure water to 5 milliliters of the colloidal silica suspension. This dilution is performed two more times. In each case, 5 milliliters of the product of the dilution step is further diluted with 45 milliliters of the ultrapure water. Thus, from the initial commercially available suspension which included 511.628 grams of colloidal silica per liter, a final dilution yields a suspension of 0.02558 grams of the colloidal silica suspension in 50 milliliters of ultrapure water.

In any event, a dilution based on a commercially available colloidal silica suspension is prepared as discussed above, and loaded into syringe 26. Then, motor 28 is actuated to step plunger 34 at a predetermined rate to the right as viewed in FIG. 1, thus to provide the colloidal silica dilution to fitting 24 at a predetermined controlled rate, preferably about $5.07 \times 10^{-3}$ milliliter per second. The dilution mingles with the ultrapure water in fitting 24, and is thoroughly mixed downstream of the fitting, due to mixing valve 36.

Assuming an ultrapure water flow rate to fitting 24 of 3.5 liters per minute, and an injection rate from syringe 26 of 0.3042 milliliters per minute, the flow out of fitting 24 is diluted to $22.5 \times 10^{-9}$ grams per milliliter, i.e. 22.5 ppb. Colloidal silica in the range from 20 to 100 ppb is required for a statistically accurate measurement of filter capture efficiency.

Thus, a first stage of the fluid flow is provided as an input to filter 18, with a fraction of the first stage provided as an input to non-volatile residue monitor 46. Accordingly, the digital output of residue monitor 46 represents the concentration of non-volatile residue in the first stage of the flow. This digital output is received by microprocessor 74, which outputs a value of the non-volatile residue concentration in terms of parts per billion, which value is displayed on terminal 78.

As the water and colloidal suspension flow through filter 18, a proportion of the colloidal silica is removed, to yield a filter output or second stage of the flow. The second stage is provided as an input to filter 20 and to non-volatile residue monitor 86. Non-volatile residue monitor 86 thus generates a digital signal to microprocessor 74, whereupon a residue value representing the non-volatile residue concentration of the second stage flow is displayed on terminal 78. The non-volatile residue concentration at the second stage is, of course, lower than such concentration of the first stage, due to the removal of at least part of the colloidal silica.

Filter 20 removes a further proportion of the colloidal silica, providing as its output a third stage of the fluid flow. A fraction of the third stage flow is provided as an input to non-volatile residue monitor 92, which provides a digital value to the microprocessor, in turn providing a third residue value to video terminal 78 for display.

Thus, microprocessor 74 provides three values for non-volatile residue concentration (in ppb) for the first, second and third stages, respectively. These values, subsequently referred to as $R_1$, $R_2$ and $R_3$, represent non-volatile residue as a whole, and do not distinguish that portion of the residue comprised of the colloidal silica suspension. Nonetheless, these values provide the basis for calculating efficiency of the filters in removing the colloidal suspension, based on the assumption that filters 18 and 20 remove only negligible proportions of dissolved impurities.

Given the above, and a further assumption that filters 18 and 20 have substantially the same efficiency (in terms of capturing colloidal silica), the non-volatile residue concentrations are employed to calculate the fractional capture efficiency of the filters. The capture efficiency can be calculated based on direct colloidal silica concentrations, if known, according to the formula:

$$E = \frac{x_1 - x_2}{x_1} = \frac{x_2 - x_3}{x_2}$$

where E is the capture efficiency, and $x_1$, $x_2$ and $x_3$ are the colloidal silica concentrations at stages one, two, and three, respectively. The non-volatile residue values displayed on terminal 78 include dissolved impurities as well as colloidal silica. Considering residue value $R_1$:

$$R_1 = x_1 + y$$

where $R_1$ is the non-volatile residue concentration at stage one, and y is the concentration of dissolved impurities at stage one. Moreover, since filters 18 and 20 are assumed to capture only the colloidal silica, the value y represents the dissolved impurity concentration at stages two and three as well Therefore, $$R_2 = x_2 + y$$

$$R_3 = x_3 + y$$

Material not captured by one of filters 18 and 20 is assumed to penetrate the filter. The fractional penetration of filters 18 and 20 can be represented based on colloidal silica concentrations, as follows:

$$P = \frac{x_2}{x_1} = \frac{x_3}{x_2}$$

Therefore, $x_2^2 = x_1 x_3$ and, by substitution:

$$(R_2 - y)^2 = (R_1 - y)(R_3 - y)$$

Therefore, $$y = \frac{R_2^2 - R_1 R_3}{2R_2 - R_1 - R_3}$$

and $$E = \frac{R_1 - R_2}{R_1 - y} = \frac{R_2 - R_3}{R_2 - y}$$

EEPROM 76 can be configured to calculate E (and y, if desired) for display on terminal 78).

In one example, the non-volatile residue monitor readings of $R_1$, $R_2$ and $R_3$ were 36.0, 19.2 and 12.0, respectively, all in terms of ppb. Accordingly, the dissolved impurity concentration (y) was 7.1 ppb, and the filter capture efficiency (E) was 0.59 (or 59%).

The above approach is particularly useful where the concentration (ppb) of dissolved impurities is substantial, compared to the concentration of colloidal silica. If the dissolved impurities are known to have a small concentration as compared to the colloidal silica concentration (for example, less than five percent of the colloidal silica), reasonably accurate determinations of filter efficiencies can be achieved employing a single filter and two non-volatile residue monitors.

Figure 7:
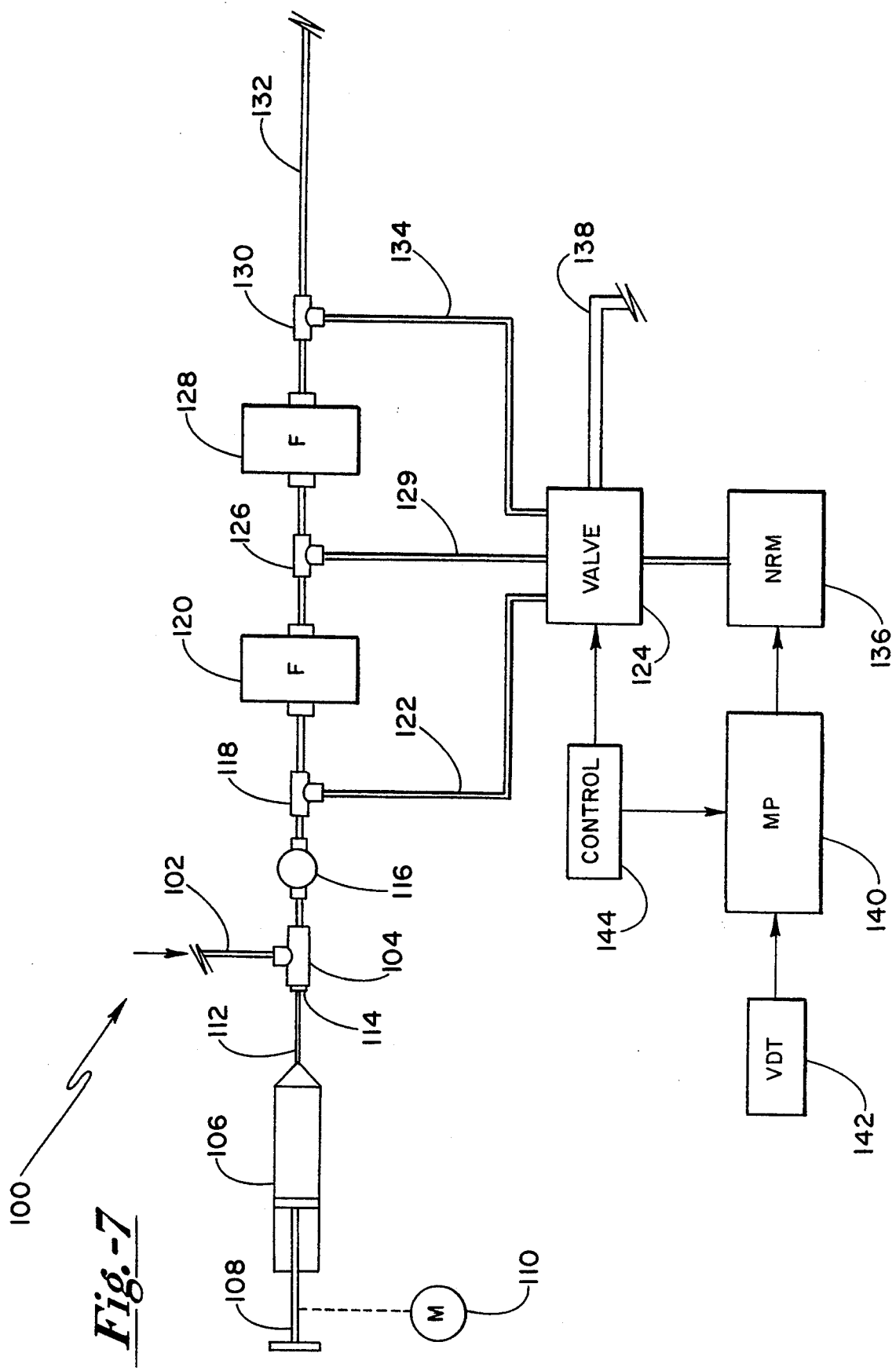
FIG. 7 is a schematic view of an alternative system for determining filter capture efficiencies in accordance with the present invention.

FIG. 7 illustrates an alternative filter testing system 100, for testing fractional capture efficiencies based on the digital output of a single non-volatile residue monitor. The system includes a conduit 102 for supplying a steady, controlled flow of ultrapure water to a T-fitting 104 in the manner previously described. A motorized syringe 106, having a plunger 108 controllably advanced by a stepper motor 110, supplies a diluted colloidal silica suspension to fitting 104 through a needle 112 accommodated by a septum 114 of the fitting. The intermingled water and dilution are thoroughly combined at a mixing valve 116 to provide a first stage flow to a fitting 118. Fitting 118 directs most of the flow downstream to a filter 120, but diverts a fraction of the first stage flow through a conduit 122 to a valve 124.

The output of filter 120 is a second stage of the flow, having a reduced concentration of the colloidal silica. A fitting 126 directs most of the second stage flow to a filter 128, while diverting a fraction of the second stage flow through a conduit 129 to valve 124. Filter 128 is substantially identical to filter 120 in terms of fractional capture efficiency. The output of filter 128, i.e. a third stage of the flow, is provided to a fitting 130 directing most of the flow to drainage, through a conduit 132. A fraction of the third stage flow travels to valve 124 through a conduit 134.

In a manner known and thus not illustrated in detail, valve 124 is selectively operated to provide any given one of the first, second and third stage flows to a non-volatile residue monitor 136, while the remaining two stages are drained through a conduit 138. The residue monitor generates a digital output based upon the non-volatile residue concentration in the flow received from valve 124. A microprocessor 140 receives the digital signal, and processes the information to generate a non-volatile residue value in parts per billion, for display on a video display terminal 142.

Valve 124 can be manually controlled, or automatically cycled to provide repeating sequences of the flow at each stage to the non-volatile residue monitor. If a controller 144 cycles the valve as shown, the controller further provides a signal to microprocessor 140 indicating which of the three stages is being provided to the residue monitor.

As compared to system 16, system 100 requires either automatic or manual cycling of flows into the non-volatile residue monitor, which precludes a simultaneous reading of all residue values. However, since the residue concentration in each of the flows remains constant, the need for cycling is a minor inconvenience in a reduced cost system that requires only one non-volatile residue monitor.

As noted above, a single filter can provide a reasonably accurate filter efficiency determination, if the concentration of dissolved impurities is small as compared to the concentration of the colloidal silica suspension. Thus in connection with system 16 in FIG. 1, only filter 18 would be employed, with readings from non-volatile residue monitor 46 and non-volatile residue monitor 86 being combined to calculate the fractional capture efficiency of filter 18. Alternatively, in connection with system 100 in FIG. 7, filter 120 would be employed in cooperation with non-volatile residue monitor 136, with valve 124 controlled to alternatively supply test liquid to the non-volatile residue monitor from upstream of the filter via conduit 122, and test liquid downstream of the filter via conduit 129. As before, R represents non-volatile residue concentration, x represents the colloidal silica concentration, and y represents the concentration of dissolved impurities. More particularly, $R_1$ and $R_2$ are the non-volatile residue monitor readings upstream and downstream of the filter, respectively. Then, since y remains constant:

$$E = \frac{R_1 - y - R_2 + y}{R_1 - y} = \frac{R_1 - R_2}{R_1 - y}$$

so long as the value of y remains small relative to the value of $R_1$ (e.g. less than 5 % of $R_1$), the quantity y can be ignored in the above equation. Therefore, the capture efficiency is determined according to the formula:

$$E = \frac{R_1 - R_2}{R_1}$$

where E is the capture efficiency, and $R_1$ and $R_2$ are the non-volatile residue monitor concentration readings upstream of the filter and downstream of the filter, respectively.

The above approach depends upon the assumption that the concentration of dissolved impurities is insubstantial, compared to the concentration of colloidal silica. Thus, two factors—the colloidal silica concentration and the timing of the test relative to preparing the colloidal silica dilution—become critical. More particularly, a commercially available colloidal silica suspension is combined with ultrapure water to prepare a colloidal silica dilution as discussed above. However, the colloidal silica concentration is kept sufficiently high to ensure that when the dilution is mixed with the ultrapure water flow, for example as at mixing valve 36 of system 16, the colloidal silica concentration x is at least 95% of the total non-volatile residue concentration R. Two principal factors determine the colloidal silica proportion downstream of valve 36: the colloidal silica concentration in the dilution; and the rate of injection of the dilution as compared to the flow of ultrapure water, e.g. at fitting 24.

The second critical factor arises because of the tendency of the colloidal silica suspension to dissolve in ultrapure water. It has been found that the colloidal silica concentration within a colloidal silica dilution diminishes over time, particularly after a day or so, because a significant portion of the colloidal silica suspension dissolves in the ultra pure water. For example, tests have shown that colloidal silica, when diluted with ultrapure water, tends to undergo substantial dissolution, given sufficient time. More particularly, Snowtex ST-40 grade colloidal silica (nominal size 11–14 nm) and Snowtex ST-XS grade colloidal silica (nominal size 4–6 nm) were diluted with ultrapure water. In both cases, the initial concentration of dissolved silica was less than 1%. After a period of 20 days, however, the solution of the Snowtex ST-40 grade colloidal silica was found to contain 12% dissolved silica, and the solution of the Snowtex ST-XS colloidal silica was found to contain 36% dissolved silica. Accordingly, it is preferable to inject the colloidal silica dilution into the ultrapure water stream for testing, within about twenty-four hours of preparing the dilution. Even more preferably, the dilution is injected substantially immediately after preparation. In any event, testing proceeds as explained above in connection with the two-filter systems.

In connection with either of systems 16 and 100, the concentration of the colloidal silica suspension as determined by the residue reading for the first stage of the flow, corresponds closely to the initial colloidal silica concentration as determined based on the colloidal silica grade utilized and the dilution procedure.

What is claimed is:

1. An apparatus for determining the efficiency of filters in removing a colloidal suspension in a liquid stream, including:

a supply means for generating a continuous liquid flow of a test liquid containing a residue at a proportion substantially uniform throughout the test liquid, said residue including a first residue component consisting of a colloidal suspension and a second residue component consisting of residue other than said colloidal suspension;

a first residue measuring means for determining the proportion of the residue in the test liquid, and for generating a corresponding first residue value;

a first filter for removing a portion of the colloidal suspension from the test liquid while allowing substantially all of the second residue component to pass through with the test liquid, and thereby providing a first filter output;

a second residue measuring means downstream of the first filter, for determining the proportion of the residue in the first filter output and for generating a corresponding second residue value;

a second filter downstream of the first filter for receiving the first filter output and removing a portion of the colloidal suspension from the first filter output while allowing substantially all of the second residue component to pass through with the test liquid, to provide a second filter output; and a third residue measuring means downstream of the second filter, for determining the proportion of the residue in the second filter output and generating a corresponding third residue value, wherein said first, second and third residue values are employable in combination to calculate the efficiency of the first filter and the second filter in removing the colloidal suspension.

2. The apparatus of claim 1 wherein:

said second residue component of the residue consists essentially of dissolved impurities that pass through the first and second filters, and wherein the first, second and third residue values further are employable in combination to calculate the proportion of the dissolved impurities in the test liquid.

3. The apparatus of claim 1 wherein:

the test liquid is ultrapure water and the colloidal suspension is colloidal silica, and wherein the supply means includes a means for generating a steady state flow of the ultrapure water and a means for injecting the colloidal silica at a steady rate into the flow of water.

4. The apparatus of claim 3 wherein:

the colloidal silica is comprised of individual particles less than about twenty nanometers in diameter.

5. The apparatus of claim 4 wherein:

the colloidal silica is injected into the flow of water at a rate predetermined to provide a proportion of the colloidal suspension, to the water, within the range of from about twenty ppb to about 100 ppb, by weight.

6. The apparatus of claim 5 wherein:
the second residue component of the residue includes impurities dissolved in the ultrapure water at a proportion to the water of less than about twenty ppb.

7. The apparatus of claim 1 wherein:
said first and second filters have substantially the same efficiency of removing the colloidal suspension.

8. The apparatus of claim 7 wherein:
the first and second filters are sub-micron pore sized filters with a high capture efficiency.

9. The apparatus of claim 1 wherein:
the first, second and third residue measuring means include respective first, second and third non-volatile residue monitors for respectively generating the first, second and third residue values as digital signals.

10. The apparatus of claim 9 further including:
a digital processing means for receiving the digital signals as inputs, and for generating an output representing filter efficiency, based on the digital inputs.

11. The apparatus of claim 1 wherein:
said first, second and third residue measuring means comprise a single non-volatile residue monitor in combination with a flow channeling means for selectively and alternatively directing one of the test liquid, first filter output and second filter output to the non-volatile residue monitor.

12. A process for determining the removal efficiency of filters, including the steps of:
producing a liquid flow of a test liquid containing a residue, said residue including a first component consisting of a colloidal suspension and a second component consisting of residue other than said colloidal suspension, the proportion of the residue being substantially uniform throughout the test liquid;
determining the proportion of the residue in the test liquid, and generating a corresponding first residue value;
using a first filter to remove a portion of the colloidal suspension from the test liquid while allowing substantially all of the second component to pass through the first filter, to produce a first filter output;
determining the proportion of the residue in the first filter output, and generating a corresponding second residue value;
using a second filter to remove a portion of the colloidal suspension from the first filter output while allowing substantially all of the second component to pass through the second filter, to produce a second filter output;
determining the proportion of the residue in the second filter output, and generating a corresponding third residue value; and
combining the first, second and third residue values to calculate the efficiency of the first filter and the second filter in capturing the colloidal suspension.

13. The process of claim 12 wherein:
the second component of the residue consists essentially of impurities dissolved in the test liquid, and the step of combining the residue values further includes calculating the proportion of the impurities in the test liquid.

14. The process of claim 13 wherein:
the steps of determining the proportion of the residue in the test liquid, in the first filter output and in the second filter output, include directing at least a portion of each of the test liquid, first filter output and second filter output respectively through a non-volatile residue monitor, thereby to generate the first, second and third values as digital signals.

15. The process of claim 12 wherein:
the step of producing a liquid flow includes generating a steady flow of ultrapure water and injecting colloidal silica into the ultrapure water, and mixing the colloidal silica and water, whereby the test liquid is the ultrapure water, and the colloidal suspension is the colloidal silica.

16. The process of claim 15 wherein:
the step of injecting the colloidal silica includes the substeps of diluting the colloidal silica in ultrapure water to a predetermined dilution; loading the diluted colloidal silica into a motorized syringe in fluid communication with the flow of ultrapure water, and controllably operating the syringe to inject the diluted colloidal silica at a constant rate into the flow of ultrapure water.

17. A process for determining the efficiency of a filter in removing a colloidal silica suspension from a liquid, including the steps of:
diluting colloidal silica in ultrapure water to provide a predetermined colloidal silica dilution;
generating a steady flow of ultrapure water;
within twenty-four hours of diluting the colloidal silica, adding the colloidal silica dilution at a constant rate into the flow of ultrapure water and mixing the colloidal silica dilution and the ultrapure water to produce a flow of test liquid in which the proportion of the colloidal silica suspension is substantially uniform and at least ninety-five percent of the total non-volatile residue concentration including the colloidal silica and dissolved impurities;
using a filter to remove a portion of the colloidal suspension from the test liquid to provide a filter output liquid;
directing portions of the test liquid and the filter output liquid through a non-volatile residue monitor, thereby to respectively generate a first digital value representing the proportion of the colloidal silica in the test liquid, and a second digital value representing the proportion of the colloidal silica in the filter output liquid; and
combining the first and second digital values to calculate the efficiency of the filter in capturing the colloidal silica suspension.

18. The process of claim 17 wherein:
the step of adding the colloidal silica dilution includes loading the colloidal silica dilution into a motorized syringe in fluid communication with the flow of ultrapure water, and controllably operating the syringe to inject the colloidal silica dilution at the constant rate.

19. The process of claim 17 wherein:
the step of directing portions of the test liquid and filter output liquid through a non-volatile residue monitor includes directing the portion of the test liquid through a first non-volatile residue monitor, and simultaneously directing the portion of the filter output liquid through a second non-volatile residue monitor, thereby to simultaneously generate the first and second digital values.

20. The process of claim 17 wherein:
the step of directing portions of the test liquid and the filter output liquid through a non-volatile residue monitor includes directing the portion of the test liquid and directing the portion of filter output liquid, alternatively, through a single non-volatile reside monitor, thereby to alternatively generate the first and second digital values.

* * * * *